(12) United States Patent
Kim et al.

(10) Patent No.: US 9,845,275 B2
(45) Date of Patent: Dec. 19, 2017

(54) METHOD FOR PREPARING POLYAROMATIC OXIDE AND POLYAROMATIC OXIDE PREPARED THEREBY

(71) Applicant: LG CHEM, LTD., Seoul (KR)

(72) Inventors: Ji Eun Kim, Daejeon (KR); Won Jae Lee, Daejeon (KR); Yong Jin Choe, Daejeon (KR); Won Jong Kwon, Daejeon (KR); Hyun Nam, Daejeon (KR); Kwon Nam Sohn, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/028,286

(22) PCT Filed: Jan. 15, 2015

(86) PCT No.: PCT/KR2015/000432
§ 371 (c)(1),
(2) Date: Apr. 8, 2016

(87) PCT Pub. No.: WO2015/111876
PCT Pub. Date: Jul. 30, 2015

(65) Prior Publication Data
US 2016/0244386 A1    Aug. 25, 2016

(30) Foreign Application Priority Data
Jan. 22, 2014  (KR) ........................ 10-2014-0007692

(51) Int. Cl.
*C07C 27/12* (2006.01)
*D01F 9/15* (2006.01)
*C10C 3/04* (2006.01)

(52) U.S. Cl.
CPC ............... *C07C 27/12* (2013.01); *C10C 3/04* (2013.01); *D01F 9/15* (2013.01)

(58) Field of Classification Search
CPC ............. C07C 27/12; C10C 3/04; D01F 9/15
See application file for complete search history.

(56) References Cited

U.S. PATENT DOCUMENTS 4,746,325 A    5/1988    Nakamura et al.

FOREIGN PATENT DOCUMENTS

| JP | 2002-285431 A | 10/2002 |
| JP | 2008-248412 A | 10/2008 |
| JP | 2011-080169 A | 4/2011 |
| JP | 05334278 B2 | 11/2013 |
| KR | 10-2008-0064571 A | 7/2008 |

OTHER PUBLICATIONS

JP2011080169, Apr. 2011, pp. 1-19; English translation.*
Fetzer, J. C. et al. "Identification of large polycyclic aromatic hydrocarbons in a coal tar pitch" Fuel vol. 74 No. 10, pp. 1533-1536, 1995.*

* cited by examiner

*Primary Examiner* — Medhanit W Bahta
(74) *Attorney, Agent, or Firm* — Dentons US LLP

(57) ABSTRACT

Disclosed are a method of preparing polyaromatic oxide and polyaromatic oxide prepared thereby, wherein the method includes (a) placing a plurality of kinds of polyaromatic hydrocarbons and water in a reactor and then stirring them; (b) increasing the temperature inside the reactor to 150 to 300° C. and then feeding a gas containing 10 wt % or more of oxygen into the reactor to increase the partial pressure of oxygen inside the reactor to 2 to 30 bar; and (c) reacting the plurality of kinds of polyaromatic hydrocarbons with oxygen to oxidize the plurality of kinds of polyaromatic hydrocarbons.

9 Claims, No Drawings

METHOD FOR PREPARING POLYAROMATIC OXIDE AND POLYAROMATIC OXIDE PREPARED THEREBY

This application is a National Stage Entry of International Application No. PCT/KR2015/000432, filed Jan. 15, 2015, and claims the benefit of Korean Application No. 10-2014-0007692, filed on Jan. 22, 2014, all of which are hereby incorporated by reference in their entirety for all purposes as if fully set forth herein.

TECHNICAL FIELD

The present invention relates to a method of preparing polyaromatic oxide and polyaromatic oxide prepared thereby and, more particularly, to a method of preparing polyaromatic oxide and polyaromatic oxide prepared thereby, in which polyaromatic oxide, resulting from oxidation treatment using a hydrothermal reaction at a high temperature and high pressure in a gas atmosphere containing at least a predetermined amount of oxygen, may be used as a dispersant for graphene.

BACKGROUND ART

A polyaromatic hydrocarbon is a compound that includes a plurality of aromatic materials such as benzene rings, etc., and is utilized as a precursor in the course of producing carbon fibers, which are used as a structural material reinforcing agent.

Conventionally, the polyaromatic hydrocarbon may be oxidized by oxidizing pitch, obtained from fossil fuel or fossil fuel products, using concentrated nitric acid ($HNO_3$), sulfuric acid ($H_2SO_4$) or a mixture thereof.

However, the preparation of polyaromatic oxide by the above conventional method is problematic because a strong acid such as nitric acid or sulfuric acid is used, which is dangerous, and also because nitrogen oxide such as NOx is produced in the course of reaction and purification, and thus related devices are required to be resistant to corrosion, undesirably increasing production costs, and furthermore, a large amount of industrial wastewater may be generated, further increasing processing costs.

For example, Japanese Patent Application Publication NO. 2008-248412 discloses a dispersant for carbon fibers, but does not describe any improvement to the conventional method of producing polyaromatic oxide.

There is a demand for a method of easily preparing polyaromatic oxide without the use of an oxidant, i.e. a strong acid.

DISCLOSURE

Technical Problem

The present invention has been made keeping in mind the above problems encountered in the related art, and an object of the present invention is to provide a method of preparing polyaromatic oxide through oxidation at a high temperature and high pressure in a gas atmosphere containing at least a predetermined amount of oxygen, without the use of an oxidant, i.e. a strong acid.

Technical Solution

In order to accomplish the above object, the present invention provides a method of preparing polyaromatic oxide, comprising: (a) placing a plurality of kinds of polyaromatic hydrocarbons and water in a reactor and then stirring them; (b) increasing a temperature inside the reactor to 150 to 300° C. and then feeding a gas containing 10 wt % or more of oxygen into the reactor to increase a partial pressure of oxygen inside the reactor to 2 to 30 bar; and (c) reacting the plurality of kinds of polyaromatic hydrocarbons with oxygen to oxidize the plurality of kinds of polyaromatic hydrocarbons.

In addition, the present invention provides polyaromatic oxide prepared by the above method.

Advantageous Effects

According to the present invention, the method of preparing polyaromatic oxide enables the easy production of polyaromatic oxide through oxidation at a high temperature and high pressure in an air atmosphere, without the use of an oxidant, that is, a strong acid.

BEST MODE

Hereinafter, a detailed description will be given of a method of preparing polyaromatic oxide and polyaromatic oxide prepared thereby, according to the present invention.

The present invention addresses a method of preparing polyaromatic oxide, comprising: (a) placing a plurality of kinds of polyaromatic hydrocarbons and water in a reactor and then stirring them; (b) increasing the temperature inside the reactor to 150 to 300° C., and then feeding a gas containing 10 wt % or more of oxygen into the reactor to increase the partial pressure of oxygen inside the reactor to 2 to 30 bar; and (c) reacting the plurality of kinds of polyaromatic hydrocarbons with oxygen to oxidize the plurality of kinds of polyaromatic hydrocarbons.

In (a) of the method of preparing polyaromatic oxide according to the present invention, the plurality of kinds of polyaromatic hydrocarbons and water are placed in the reactor and then stirred.

In (a), the polyaromatic hydrocarbons, which are added into the reactor together with water, are not particularly limited, and preferably useful are polyaromatic hydrocarbons having a molecular weight of 200 to 1500. Also, the polyaromatic hydrocarbons are not particularly limited, and preferably include 5 to 50 benzene rings. The polyaromatic hydrocarbons may include pitch obtained from fossil fuel or fossil fuel products satisfying the above conditions. Particularly useful is a carbonaceous mixture including polyaromatic hydrocarbons.

The reactor is not particularly limited, and is preferably a hydrothermal reactor.

In (b) of the method of preparing polyaromatic oxide according to the present invention, the temperature inside the reactor is increased to 150 to 300° C., and a gas containing 10 wt % or more of oxygen is then fed into the reactor, so that the partial pressure of oxygen inside the reactor is increased to 2 to 30 bar.

In (a), the temperature inside the reactor is elevated to 150 to 300° C. and the high temperature is maintained, and simultaneously, the gas containing oxygen ($O_2$) is added, whereby the partial pressure of oxygen inside the reactor is maintained at a high pressure of 2 to 30 bar while feeding oxygen ($O_2$) into the reactor. If the temperature inside the reactor is lower than 150° C., oxidation may not be efficiently carried out, and the oxygen content of the polyaromatic oxide may not be sufficient. In contrast, if the temperature inside the reactor is higher than 300° C., the additional effect resulting from the increased temperature may become insignificant. Also, the gas fed into the reactor may contain oxygen in an amount of 10 wt % or more, preferably 20 to 100 wt %, and more preferably 20 to 60 wt %. If the oxygen content is less than 10 wt %, oxidation may not be efficiently carried out, and oxidation ability due to the addition of gas may deteriorate. Also, if the pressure inside the reactor is below 2 bar, oxidation may not be efficiently carried out, and the oxygen content of the polyaromatic oxide may not be sufficient. On the other hand, if the pressure inside the reactor exceeds 30 bar, the additional effect resulting from the increased pressure may become insignificant.

In (c) of the method of preparing polyaromatic oxide according to the present invention, the plurality of kinds of polyaromatic hydrocarbons may be reacted with oxygen and thus oxidized.

In conventional methods of preparing polyaromatic oxide, polyaromatic hydrocarbons are oxidized using a strong acid such as nitric acid or sulfuric acid or an additional oxidant. However, in (c) according to the present invention, the polyaromatic hydrocarbons may be oxidized through the reaction with oxygen at a high temperature and high pressure. The reaction of (c) is preferably carried out for 3 to 15 hr. If the reaction time is shorter than 3 hr, oxidation may be insufficient, and the oxygen content of the oxide may be decreased. In contrast, if the reaction time is longer than 15 hr, there is no significant effect resulting from the increased reaction time.

The method of preparing polyaromatic oxide according to the present invention may further comprise (d) cooling.

In (d), cooling may be performed rapidly, and preferably the reactor is cooled to 30 to 80° C. within 10 to 30 min.

The method of preparing polyaromatic oxide according to the present invention may further comprise (e) purification.

In (e), purification may be performed by purifying the product cooled in (d), thus obtaining a mixture comprising the plurality of kinds of polyaromatic hydrocarbon oxides.

The purification method is not particularly limited, but the oxide product may be purified through centrifugation.

The present invention addresses polyaromatic oxide prepared by the method.

The polyaromatic oxide thus obtained may contain oxygen in an amount of 5 to 20 wt %, and preferably 10 to 17 wt %, based on the total amount of the oxide.

The polyaromatic oxide thus obtained is not particularly limited, and may be used as a dispersant for a hydrocarbon compound or derivatives thereof. The hydrocarbon compound may include any one or more selected from among carbon nanotubes, graphene, and graphite.

Mode for Invention

A better understanding of the present invention may be obtained via the following examples, which are merely set forth to illustrate the present invention, and those skilled in the art will appreciate that various changes and modifications are possible, without departing from the scope and spirit of the invention as disclosed in the accompanying claims.

EXAMPLE

Preparation of Polyaromatic Oxide

Example 1

0.9 g of pitch (made by Posco) and 150 g of distilled water were placed in a hydrothermal reactor (U-20040624, UTO systems) made of Hastelloy and equipped with a magnetic stirrer, and were then stirred. The temperature inside the reactor was elevated to 200° C., after which compressed air having an oxygen content of 20 wt % was fed into the reactor until the partial pressure of oxygen inside the reactor was 4 bar. The hydrothermal reaction was carried out for 13 hr, and cooling water was injected through the tube provided in the reactor so that the reaction product was rapidly cooled to 50° C. within 30 min. Subsequently, the dispersant was recovered using a filter, followed by drying in a vacuum oven at 100° C. for 15 hr, yielding a polyaromatic oxide.

Example 2

A polyaromatic oxide was prepared in the same manner as in Example 1, with the exception that the pitch was used in an amount of 2 g and the hydrothermal reaction was carried for 4 hr.

Comparative Example 1

A polyaromatic oxide was prepared in the same manner as in Example 1, with the exception that the pitch was used in an amount of 2 g, together with 200 g of distilled water, and the hydrothermal reaction was carried for 2 hr under the condition that the temperature inside the reactor was set to 130° C.

Comparative Example 2

The pitch used in the above examples was used without change.

Test Example 1 mg of each of the polyaromatic oxide samples of Examples 1 and 2 and Comparative Example 1 and the pitch sample of Comparative Example 2 was placed on foil and heated from 900° C. to 1500° C. The gas was generated from each sample through the heating, collected, and then measured for elemental analysis using an elemental analyzer (Flash 2000, Thermo Fisher Scientific), whereby the amounts of carbon, oxygen, hydrogen, and nitrogen in the gas were determined. The results are shown in Table 1 below.

TABLE 1

| | C (wt %) | H (wt %) | N (wt %) | O (wt %) |
|---|---|---|---|---|
| Ex. 1 | 75.8 | 3.2 | — | 16.3 |
| Ex. 2 | 85.1 | 3.7 | — | 11.3 |
| C. Ex. 1 | 91 | 4.6 | — | 4.3 |
| C. Ex. 2 | 95.5 | 4.5 | — | — |

As is apparent from Table 1, the polyaromatic oxides of Examples 1 and 2 according to the present invention had oxygen contents of 16.3 wt % and 11.3 wt %, respectively, which are observed to be much higher than those of Comparative Example 1, having an oxygen content of 4.3 wt %, and Comparative Example 2, in which no oxygen was detected.

The invention claimed is:
1. A method of preparing a polyaromatic oxide, comprising:

(a) placing a plurality of kinds of polyaromatic hydrocarbons and water in a reactor and then stirring the plurality of kinds of polyaromatic hydrocarbons and water;

(b) increasing a temperature inside the reactor to 150 to 300° C. and then feeding a gas containing 10 wt % or more of oxygen into the reactor to increase a partial pressure of oxygen inside the reactor to 2 to 30 bar; and (c) reacting the plurality of kinds of polyaromatic hydrocarbons with oxygen to oxidize the plurality of kinds of polyaromatic hydrocarbons, while maintaining the temperature and the partial pressure of oxygen.

2. The method of claim 1, wherein in (b), the gas contains oxygen in an amount of 20 to 100 wt %.

3. The method of claim 1, wherein the polyaromatic hydrocarbons have a molecular weight ranging from 200 to 1500.

4. The method of claim 1, wherein the polyaromatic hydrocarbons include 5 to 50 benzene rings.

5. The method of claim 1, wherein the polyaromatic hydrocarbons comprise pitch obtained from fossil fuel or fossil fuel products.

6. The method of claim 1, further comprising (d) cooling the reactor, thus obtaining a cooled product, after (c).

7. The method of claim 6, further comprising (e) purifying the cooled product, thus obtaining a mixture comprising a plurality of kinds of polyaromatic hydrocarbon oxides.

8. The method of claim 1, wherein the polyaromatic oxide is used as a dispersant for a hydrocarbon compound or derivatives thereof.

9. The method of claim 8, wherein the hydrocarbon compound comprises any one or more selected from the group consisting of carbon nanotubes, graphene, and graphite.

\* \* \* \* \*